United States Patent
Ito et al.

(10) Patent No.: US 7,285,095 B2
(45) Date of Patent: Oct. 23, 2007

(54) METHOD OF ANALYZING AND DISPLAYING BLOOD VOLUME USING MYOCARDIAL BLOOD VOLUME MAP

(75) Inventors: Hiroshi Ito, 1-25 H-612 Kamishinden, Toyonaka-city, Osaka (JP) 560-0085; Yasuhiro Nakajima, Ikoma (JP)

(73) Assignees: YD, Ltd., Ikoma (JP); ME, Co., Ltd., Nagano (JP); Hiroshi Ito, Toyonaka (JP)

( * ) Notice: Subject to any disclaimer, the term of this patent is extended or adjusted under 35 U.S.C. 154(b) by 846 days.

(21) Appl. No.: 10/742,836

(22) Filed: Dec. 23, 2003

(65) Prior Publication Data

US 2004/0138567 A1 Jul. 15, 2004

(30) Foreign Application Priority Data

Dec. 27, 2002 (JP) ............................. 2002-379760

(51) Int. Cl.
*A61B 8/14* (2006.01)
(52) U.S. Cl. ..................................................... 600/458
(58) Field of Classification Search ................ 600/315, 600/407, 410, 431, 437, 440, 443, 447–450, 600/458, 467; 424/9, 9.52, 11; 324/325; 73/602, 626; 382/128
See application file for complete search history.

(56) References Cited

U.S. PATENT DOCUMENTS

| | | | | |
|---|---|---|---|---|
| 5,425,366 A | * | 6/1995 | Reinhardt et al. | 600/458 |
| 5,732,707 A | * | 3/1998 | Widder et al. | 600/458 |
| 5,743,266 A | * | 4/1998 | Levene et al. | 600/458 |
| 6,015,384 A | * | 1/2000 | Ramamurthy et al. | 600/440 |
| 6,080,107 A | * | 6/2000 | Poland | 600/458 |
| 6,217,520 B1 | * | 4/2001 | He et al. | 600/467 |
| 6,224,553 B1 | * | 5/2001 | Nevo | 600/437 |
| 6,315,730 B1 | * | 11/2001 | Hoff et al. | 600/458 |
| 2002/0028994 A1 | * | 3/2002 | Kamiyama | 600/437 |
| 2003/0013963 A1 | * | 1/2003 | Bjaerum et al. | 600/443 |
| 2003/0153823 A1 | * | 8/2003 | Geiser et al. | 600/407 |
| 2004/0081623 A1 | * | 4/2004 | Eriksen et al. | 424/9.52 |
| 2004/0143189 A1 | * | 7/2004 | Lysyansky et al. | 600/450 |

OTHER PUBLICATIONS

Nagashima et al., "Novel Method for Myocardial Contrast Echocardiography Using LevovistTM : Usefulness of Myocardial Blood Volume Map For Diagnosing Ischemic Heart Disease." Circulation Journal : Official Journal of the Japanese Circulation Society., vol. 69, No. Supplemnt_I(20050301), p. 238.*

(Continued)

*Primary Examiner*—Thao X. Le
*Assistant Examiner*—Salieu M Abraham
(74) *Attorney, Agent, or Firm*—Oblon, Spivak, McClelland, Maier & Neustadt, P.C.

(57) ABSTRACT

A contrast echo image of the myocardium and a cardiac chamber obtained by use of ultrasound diagnostic equipment is analyzed so as to determine the volume of blood within the myocardium. The contrast echo image is divided into a plurality of calculation regions, each being considered to have a uniform acoustic field intensity and covering a portion of a myocardium image region and a corresponding portion of a cardiac chamber image region. For each calculation region, a difference in intensity between the myocardium image region and the cardiac chamber image region is obtained, and the myocardium image region is colored in accordance with the difference.

7 Claims, 10 Drawing Sheets

OTHER PUBLICATIONS

Villanueva et al., "Myocardial Contrast Echocardiography Can Be Used to Quantify Intramyocardial Blood Volume: □□New Insights Into Structural Mechanisms of Coronary Autoregulation." Circulation, vol. 96, pp. 1004-1011 (1997).*

Janardhanan et al., "Myocardial Contrast Echocardiography: A New Tool for Assessment of Myocardial Perfusion." Indian Heart Journal, vol. 57, pp. 210-216 (2005).*

* cited by examiner

HIGH BLOOD QUANTITY PORTIONS AND LOW BLOOD QUANTITY PORTIONS OF MYOCARDIUM ARE DISPLAYED IN WARM COLORS AND COLD COLORS, RESPECTIVELY

METHOD OF ANALYZING AND DISPLAYING BLOOD VOLUME USING MYOCARDIAL BLOOD VOLUME MAP

BACKGROUND OF THE INVENTION

1. Field of the Invention

The present invention relates to a contrast echo image analysis method employed for detection or treatment of ischemic heart diseases or similar diseases, in which a contrast echo image of the myocardium and cardiac chambers—which image is obtained by use of ultrasound diagnostic equipment after injection of a microbubble ultrasound contrast agent into blood vessel—is analyzed so as to visually and quantitatively determine the volume of blood flowing through the myocardium on the basis of intensity values of the myocardium region and the cardiac chamber regions of the image.

2. Background Art

X-ray diagnostic equipment, X-ray CT equipment, MRI equipment, or nuclear medical diagnostic equipment enables diagnosis of interior tissues of a human body without surgical operation, but such equipment involves the following problems: a subject is exposed to X-rays or nuclear radiation, and examination requires a long period of time. Meanwhile, catheterization is an invasive examination technique in which a catheter is inserted into a blood vessel. In contrast, ultrasound diagnostic equipment, which employs ultrasound waves, causes virtually no adverse effects on body tissues of a subject—which would otherwise be incurred through exposure of the subject to X-rays, nuclear radiation, or magnetic field during use of the aforementioned equipment; i.e., ultrasound diagnostic equipment is non-invasive diagnostic equipment. Ultrasound diagnostic equipment attains real-time image display, involves low risk even when repeatedly used within a short period of time, and enables examinations to be completed within a short period of time. Furthermore, ultrasound diagnostic equipment is small in size and is inexpensive, and thus can be used in any hospital. In addition, such ultrasound diagnostic equipment allows a medical doctor to readily and thoroughly examine a region of interest (ROI) while directly operating the equipment.

When ultrasound diagnostic equipment is used, an ultrasound probe is placed on the body surface in order to receive reflection waves of ultrasound waves emitted from a transducer, and tomographic images of body tissues are obtained on the basis of the received reflection waves. Therefore, for example, the state of the heart, the abdomen, or the mammary gland, or movement of a fetus within the uterus can be observed in real time. Meanwhile, through use of the power Doppler method, imaging of the blood flow can be performed.

The blood that has circulated throughout the body flows through veins to the right atrium and the right ventricle, and then flows from the right ventricle through arteries to the lungs. The blood is oxygenated in the lungs. The blood that has been oxygenated in the lungs passes through the left atrium and the left ventricle, and flows through arteries to the entire body. During this circulation, a portion of the thus-oxygenated blood is fed to coronary arteries, which are branching from the aorta. The coronary arteries, which cover the myocardium while forming a web-like network, supply oxygen and nutrients, which energize the heart, to the myocardium. When the coronary arteries are occluded or stenosed due to formation of thrombi or occurrence of coronary artery disorder, the amount of the blood supplied to the heart is reduced, causing adverse effects on action of the heart. When the coronary arteries are occluded, and necrosis of myocardial cells occurs, the contraction force of the myocardial cells is lost. This symptom is called "myocardial infarction." When the amount of the blood supplied to the myocardium is reduced as a result of narrowing of the coronary arteries, although occlusion of the arteries does not occur, the heart is adversely affected. This symptom is called "angina pectoris." Myocardial infarction and angina pectoris are collectively called "ischemic heart diseases."

In the case where the heart is examined by use of ultrasound diagnostic equipment, a contrast agent is injected via a vein in order to evaluate blood perfusion, because the intravenous injection of a contrast agent is less invasive. In diagnosis by use of a contrast agent, change with time in spatial distribution of the contrast agent in a site to be diagnosed is observed on the basis of an increase in an intensity-enhanced area and an increase in intensity. In addition, there is obtained the transit time between the injection of the contrast agent and the arrival thereof to a region of interest (ROI), as well as the time intensity curve (TIC), which represents change with time in intensity of an echo image of the ROI captured by use of a contrast agent.

Ultrasound waves (echo signals) reflected from an organ of a living organism tend not to exhibit non-linear behaviors. However, echo signals obtained by use of an ultrasound contrast agent predominantly containing microbubbles include non-fundamental wave components attributable to non-linear behaviors. Therefore, when only the non-fundamental wave components are separated from the echo signals and detected, an organ of a living organism and a cavity (e.g., the interior of a blood vessel or the cardiac chambers of the heart) can be observed at a high contrast ratio in an image generated by a contrast agent.

The aforementioned contrast echo method is disclosed in, for example, Japanese Patent Application Laid-Open (kokai) No. 11-155858 (title of the invention: "Ultrasound Diagnostic Equipment and Ultrasound Diagnostic Method") and Japanese Patent Application Laid-Open (kokai) No. 2001-178722 (title of the invention: "Ultrasound Diagnostic Equipment and Ultrasound Diagnostic Method"). The former patent document discloses a method for obtaining a more effective contrast echo image, in which the transmission sound pressure of ultrasound pulses is optimized in order to increase the intensity of an image obtained by use of a contrast agent. The latter patent document discloses a method and equipment for reducing labor or burden of an operator when carrying out a contrast echo method employing an ultrasound contrast agent predominantly containing microbubbles. This patent document proposes a method for informing a diagnostician of vanishment of microbubbles in the form of sound information, by use of a speaker.

In the case where the heart is examined by use of ultrasound diagnostic equipment and in accordance with the contrast echo method employing an ultrasound contrast agent predominantly containing microbubbles, a high level of skill is required for diagnosing ischemic heart diseases (e.g., myocardial infarction and angina pectoris) on the basis of the resultant contrast echo images. The reasons for this are described below.

When a microbubble ultrasound contrast agent is injected into blood vessels, and an ultrasound probe is placed on the body surface to thereby apply to a region of interest (ROI) ultrasound waves transmitted from the probe, the ultrasound waves are reflected by microbubbles contained in the contrast agent. Ultrasound waves of high energy are reflected from a site where blood containing the contrast agent is present. When received reflective waves are converted into intensity and an image is displayed on the basis of the intensity, a portion of the image corresponding to such a site is displayed with a higher intensity; i.e., as a bright region. A site to which the contrast-agent-containing blood is not supplied in a sufficient quantity is displayed with a lower intensity; i.e., as a dark region. Therefore, whether or not the blood is sufficiently supplied to the myocardium can be determined through comparison of the intensity of the myocardium at different locations.

Ultrasound waves transmitted from the probe attenuate with the distance between the body surface and a relevant site of the body; i.e., the depth of the site. Further, since the probe focuses ultrasound waves on a relevant site, the energy level at that site becomes higher than that of other sites. Moreover, in the case where a color image of the heart is obtained by means of the power Doppler method or the B-mode method, the color of image regions corresponding to the cardiac chambers bleeds into an image region corresponding to the myocardium. Therefore, difficulty is encountered in correctly determining the state of perfusion of blood on the basis of contrast echo images of the myocardium and the cardiac chambers.

As described above, in the case of a conventional contrast echo image, intensity varies from site to site because of depthwise attenuation of ultrasound waves and energy maximization at a site where ultrasound waves are focused. However, in the conventional image processing technique, intensity measurement is performed without correction of variation in intensity, which variation occurs due to the difference in acoustic field or focusing of ultrasound waves. Therefore, in the conventional technique, difficulty is encountered in determining whether the difference in intensity between different sites in the cardiac chambers or the myocardium is caused by the difference in acoustic field or by the difference in perfusion.

Meanwhile, diagnosing the state of perfusion of the cardiac chambers or the myocardium on the basis of a contrast echo image of the heart depends on the skill of a diagnostician, and an unskilled diagnostician encounters difficulty in correctly diagnosing such perfusion in a simple manner. This is because image processing has not conventionally been performed objectively, and quantitative analysis of the contrast echo image has not been carried out.

SUMMARY OF THE INVENTION

In view of the foregoing, an object of the present invention is to provide a method for analyzing blood perfusion within the myocardium on the basis of a contrast echo image obtained by use of ultrasound diagnostic equipment, to thereby provide a diagnostician with data for visually and quantitatively determining the perfusion.

In order to attain the aforementioned object, in the present invention, the below-described medical facts are taken into consideration.

1) The cardiac chambers (the atriums and the ventricles) are filled with blood.

2) In general, blood perfusion disorder tends to occur on the endocardial side of the myocardium, rather than on the epicardial side thereof.

A contrast echo image obtained by use of ultrasound diagnostic equipment involves the following problems.

a) In the case where a color image is obtained by means of a power Doppler mode, the color of image regions corresponding to the cardiac chambers may bleed toward an image region corresponding to the myocardium.

b) The intensity of a contrast echo image varies in accordance with a depthwise change in acoustic field intensity and distance from the top.

c) The intensity varies from site to site due to noise.

The present invention solves the aforementioned problems by dividing images of the myocardium and the cardiac chambers into image regions which are considered to have the same acoustic field intensity, and comparing and studying the image regions.

Specifically, the present invention provides a method of analyzing a contrast echo image of the myocardium and a cardiac chamber so as to determine the state of blood perfusion in the myocardium, the contrast echo image being obtained by use of ultrasound diagnostic equipment after injection of a microbubble ultrasound contrast agent into blood vessels, and including a myocardium image region corresponding to the myocardium and a cardiac chamber image region corresponding to the cardiac chamber. During the analysis, the contrast echo image is finely divided into a plurality of calculation regions, each being considered to have a uniform acoustic field intensity and covering a portion of the myocardium image region and a corresponding portion of the cardiac chamber image region. For each calculation region, a difference in intensity between the myocardium image region and the cardiac chamber image region is obtained, and the myocardium image region is colored in accordance with the difference. This is the basic procedure of a blood volume analyzing method of the present invention which utilizes a myocardial blood volume map (MBVM). The MBVM refers to a map showing distribution of blood volume within the myocardium; i.e., an image of the myocardium which is colored in accordance with the state of blood perfusion within the myocardium.

In the present invention, the state of blood perfusion within the myocardium is quantized by the following method. In the blood volume analyzing method using an MBVM, a power P is first obtained by the following equation:

$$10 \log_{10} P = I_1 - I_2$$

where $I_1$ represents the intensity of a myocardium image region, $I_2$ represents the intensity of a cardiac chamber image region.

Subsequently, a current blood volume V (unit: ml/100 g: blood volume) in the myocardium in a region of interest is calculated by the following equation:

$$V = 100 \times P \text{ (ml/100 g)}.$$

The present invention employs the following three methods in order to obtain an MBVM. First, an equal-interval sliding window method will be described. On an original contrast echo image, the endocardial, which is a boundary between the myocardium and a cardiac chamber, and the epicardial are traced to thereby form an endocardial line and an epicardial line, respectively, and then an inner line and an outer line are drawn on the inner and outer sides, respectively, of the endocardial line in such a manner that each of the inner line and the outer line extends along the endocardial line while separated therefrom by a distance d2 (1 to 20 mm).

Subsequently, two boundary lines (acoustic field lines) are drawn at an interval d1 (1 to 20 mm) in order to obtain a region considered to have a uniform acoustic field intensity. A region surrounded by the endocardial line, the inner line, and the acoustic field lines is defined as a cardiac chamber calculation region, and a region surrounded by the endocardial line, the outer line, and the acoustic field lines is defined as a myocardium calculation region. The average intensity of the cardiac chamber calculation region is subtracted from the average intensity of the myocardium calculation region to thereby obtain a luminous difference. Subsequently, a color corresponding to the luminous difference is selected from a color table, and the entirety of a myocardium image region sandwiched between the acoustic field lines is colored with the selected color.

The above-described difference calculation is repeated, while the two acoustic field lines are shifted by the interval d1. The reason why the interval of the acoustic field lines is set to d1 and the average intensity of each calculation region is used is to minimize influence of noise. Further, the color of the entire myocardium image region is colored in accordance with the luminous difference of the myocardium calculation region in consideration of the facts that in some cases precise intensity data are not obtained in the vicinity of the epicardial, and that a blood perfusion disorder tends to occur from the vicinity of the endocardial.

In an overlap sliding window method, a contrast echo image is finely divided into calculation regions in a manner that is basically the same as that used in the equal-interval sliding window method. However, the overlap sliding window method differs from the equal-interval sliding window method in the following points. In order to further reduce the influence of variation in acoustic field intensity, every time the intensity difference between the myocardium calculation region and the cardiac chamber calculation region is calculated for coloring the myocardium calculation region, the acoustic field lines are shifted by a small distance d3 (e.g., d3=0.5 mm) along a vertical axis perpendicular to the acoustic field lines. In this method, since the shifting distance is small, the calculation regions partially overlap. The overlap portion of the preceding calculation region is colored by a new color corresponding to the calculation value (intensity difference) of the succeeding calculation region. The reason while the vertical dimension of each calculation region is set to d1 despite the shifting distance being set to d3, which is smaller than d1, is to eliminate influence of noise (the influence of noise increases as the area of each calculation region decreases).

In a pixel-by-pixel method as well, a contrast echo image is finely divided into calculation regions in a manner that is basically the same as that used in the equal-interval sliding window method. However, the pixel-by-pixel method differs from the equal-interval sliding window method in the following points. That is, the intensity is calculated for each of pixels within a region surrounded by the endocardial line, the epicardial line, and two acoustic field lines; the difference between the intensity of each pixel and the average intensity of the cardiac chamber calculation region is obtained; and each pixel is colored by a color corresponding to the difference. This method enables evaluation of an original contrast echo image as it is within a range from the endocardial to the epicardial of the myocardium. However, a portion of the myocardium image region containing noise or an unclear portion in the vicinity of the epicardial are displayed as they are.

In the case where a color image of the heart is obtained by means of the power Doppler method, the color of the cardiac chamber image region (blooming) often bleeds into a myocardium image region, which hinders accurate measurement of the myocardium. In order to eliminate the influence of such color bleeding, there is provided means for drawing first and second buffer lines on the inner side and outer side, respectively, of the endocardial line in such a manner that each of the buffer lines extends along the endocardial line while being separated from the endocardial line by a predetermined distance d4, and defining, as calculation regions, a region surrounded by two acoustic field lines, the first buffer line, and the inner line, and a region surrounded by the two acoustic field lines, the second buffer line, and the outer line. The value of the distance d4 can be adjusted, or increased and decreased in increments of 0.5 mm.

BRIEF DESCRIPTION OF THE DRAWINGS

Various other objects, features and many of the attendant advantages of the present invention will be readily appreciated as the same becomes better understood by reference to the following detailed description of the preferred embodiment when considered in connection with the accompanying drawings, in which.

DETAILED DESCRIPTION OF PREFERRED EMBODIMENT

An embodiment of the present invention will be described with reference to the appended drawings. In the present invention, the state of blood perfusion of the myocardium is analyzed on the basis of contrast echo images obtained by use of ultrasound diagnostic equipment. A computer unit is employed as hardware for analysis. Contrast echo images obtained by use of ultrasound diagnostic equipment are stored in a high-capacity external storage medium such as a CD or MO, and image analysis is performed by use of the thus-stored images.

Figure 1:
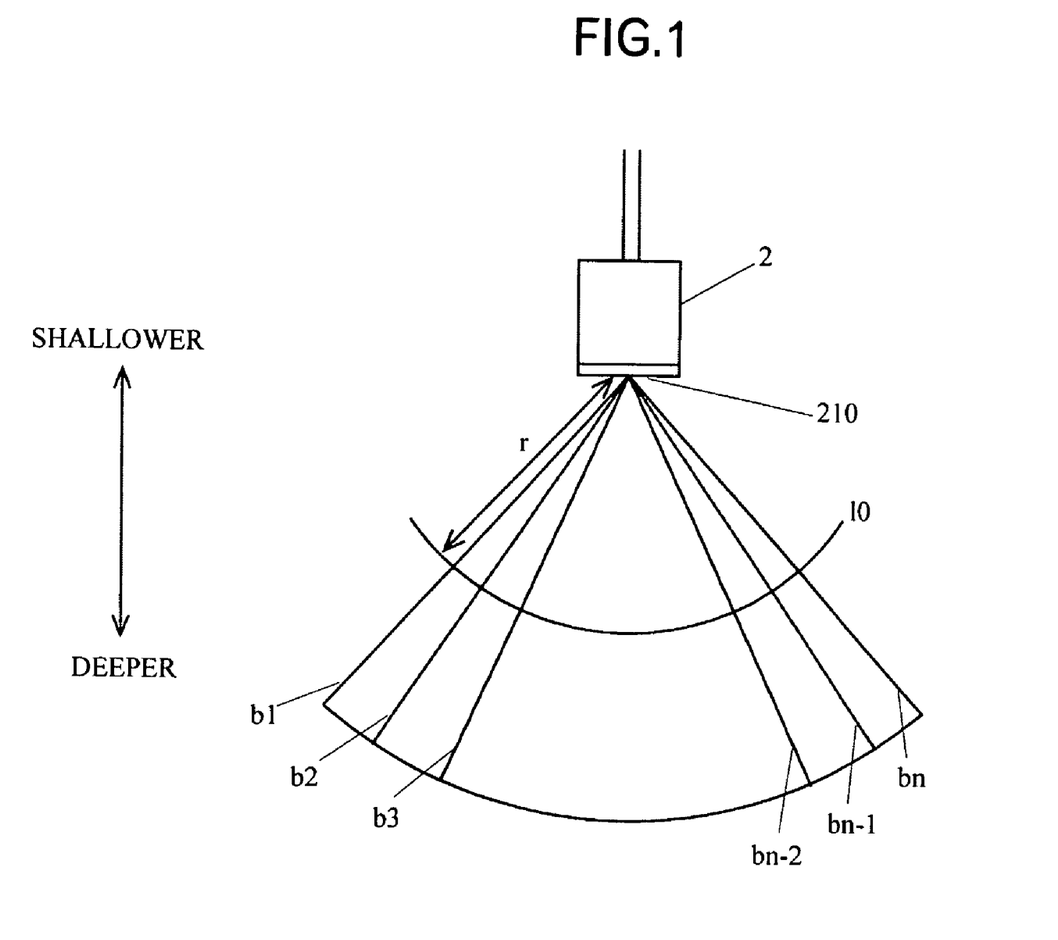
FIG. 1 is a diagram of an ultrasound scanning beam showing a method of obtaining contrast echo images by use of an ultrasound probe.

FIG. 1 shows scanning of the body by use of an ultrasound probe. Ultrasound beams b1, b2, . . . bn which are transmitted (actually, continuously transmitted) from a tip portion 210 of an ultrasound probe 2 applied to the body surface are reflected by an object, and the thus-reflected waves are received by the probe 2. The thus-received waves are converted to a digital contrast echo image, which is then stored in a memory or a storage device. In FIG. 1, an upward direction corresponds to a direction toward the body surface, and a downward direction corresponds to a direction toward the center of the body. The received reflection waves (echo) are converted into intensity data, and the data are transformed into color image data in the case of, for example, the power Doppler method. The same acoustic field intensity (ultrasound intensity) is attained at locations a distance (r) away from the tip portion 210. In FIG. 1, reference numeral 10 denotes a line connecting locations having the same acoustic field intensity (hereinafter, the line will be referred to as an "acoustic field line").

In an ultrasound echo image, intensity decreases depthwise (toward the downward direction in FIG. 1). Meanwhile, the energy of ultrasound waves becomes the highest in the vicinity of the focal point. Therefore, when an echo image is displayed by use of the absolute values of intensity data as in the case of a conventional technique, the resultant image fails to be correctly evaluated. In the present invention, every portion of an image region corresponding to the myocardium (hereinafter referred to as a "myocardium image region") is colored in accordance with the difference in intensity between that portion and a corresponding portion of an image region corresponding to the cardiac chamber (hereinafter referred to as a "cardiac chamber image region"), these portions corresponding to portions of the myocardium and the cardiac chamber which are considered to have the same acoustic field intensity. A specific procedure for coloring the myocardium image region will be described below. The below-described procedure can be applied to a monochromic image obtained by means of the third harmonic method, the 1.5 harmonic method, or a similar method, as well as to an image obtained by means of the power Doppler method. This is because analysis is performed by use of merely intensity data.

Figure 2:
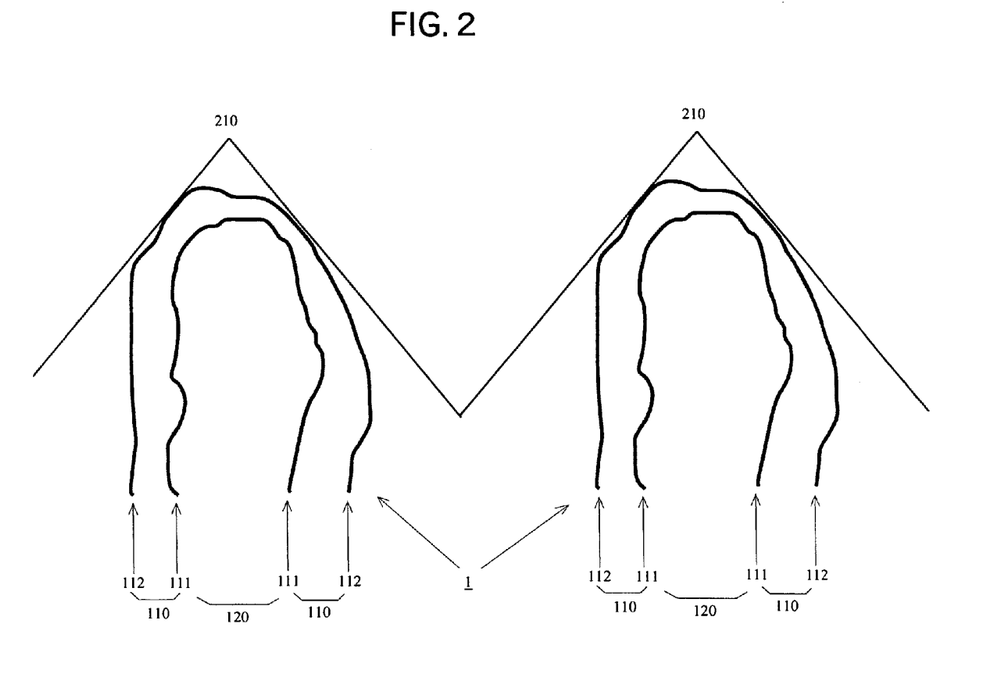
FIG. 2 is a schema showing contrast echo images.

FIG. 2 shows an example of a contrast echo image of the myocardium and a cardiac chamber. Such a contrast echo image is obtained in the form of a color image (in the case of the power Doppler method), or in the form of a monochromic image (in the case of the third harmonic method or the 1.5 harmonic method). The contrast echo image is captured at the below-described timing. A microbubble ultrasound contrast agent is injected through the veins. Although the contrast agent may be injected through the arteries, in general, the contrast agent is injected through the veins, since intravenous injection is less invasive. The contrast echo image is captured at the timing when the contrast agent is considered to have reached a region of interest and the region is considered to have been sufficiently filled with the contrast agent. In the case where a contrast echo image of the heart is captured, the contrast echo image can be captured at a timing as determined on the basis of the waveform of an electrocardiogram.

Some ultrasound diagnostic equipment capture two images of the region of interest at such a timing. The first image is captured immediately after the region of interest has been filled with the contrast agent, and the second image is captured when a predetermined period of time (about 100 msec) has elapsed after the capture of the first image. When ultrasound waves hit the ultrasound contrast agent containing microbubbles, most of the microbubbles vanish. Therefore, through comparison between the first and second images, the state of noise of the first image can be determined, along with whether the ultrasound contrast agent fills the region of interest as expected. For example, when the first and second images are identical with each other, the first image may have been captured before the ultrasound contrast agent had reached the region, which means that the captured images cannot be used for analysis. The left-hand image in FIG. 2 is the first-captured image, and the right-hand image in FIG. 2 is the second-captured image.

Figure 3:
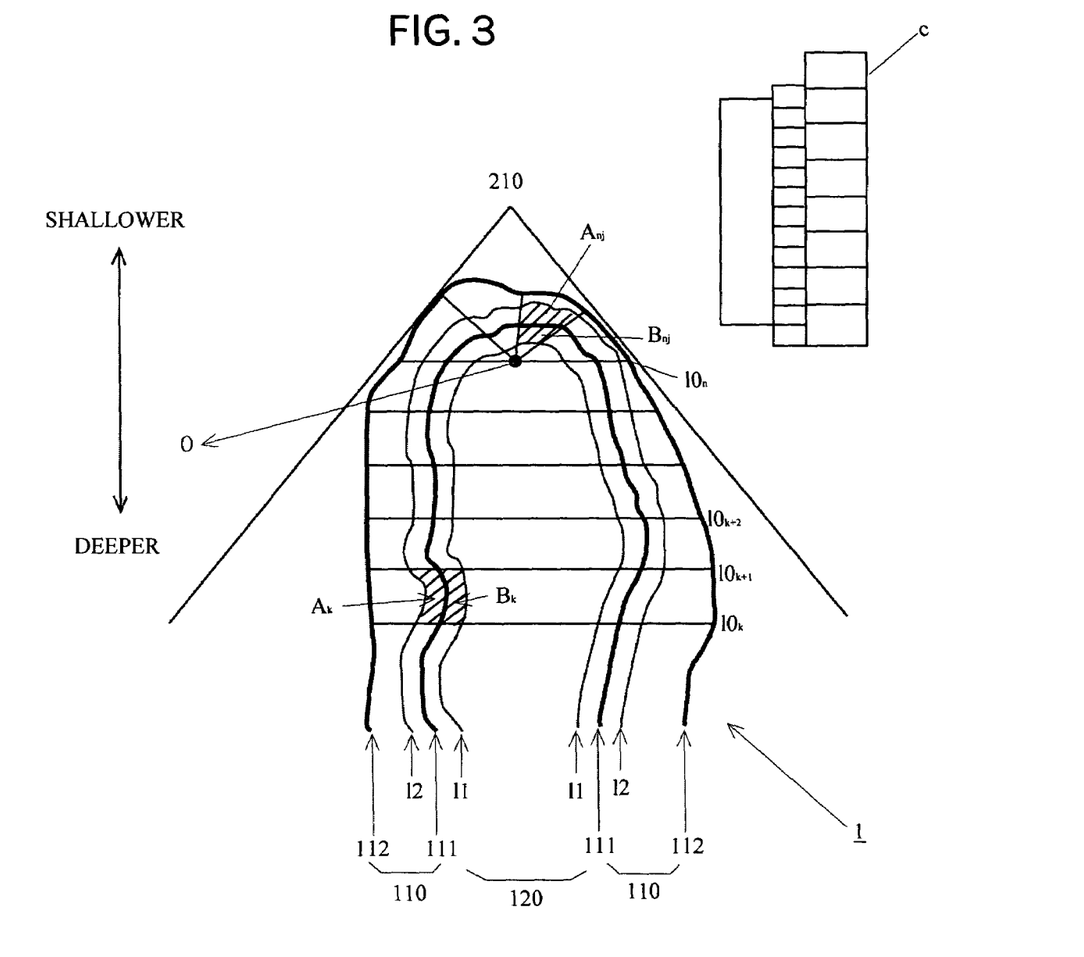
FIG. 3 is a cross sectional view of the heart (the myocardium and a cardiac chamber) to be used for explaining an equal-interval sliding window method of the present invention (an example in which the heart is equally divided in the depth direction by use of straight lines)

FIG. 3 shows an image which corresponds to that of FIG. 2 and on which contours of the endocardial and the epicardial and boundary lines (acoustic field lines) are drawn. The contours are manually input by use of a suitable device such as a mouse. A contour representing the endocardial will be referred to as an "endocardial line," and a contour representing the epicardial will be referred to as an "epicardial line." Coloring of a myocardium image region in an equal-interval slide window method is performed by the following steps:

1) On an original contrast echo image, a region corresponding to the endocardial 111 and a region corresponding to the epicardial 112 are traced to thereby form an endocardial line and an epicardial line, respectively. A region between the endocardial line and the epicardial line corresponds to the myocardium 110. This tracing step is performed manually; however, the remaining steps are automatically performed by means of a program.

2) An inner line 11 and an outer line 12 are drawn on the inner and outer sides, respectively, of the endocardial line 111 in such a manner that each of the inner line 11 and the outer line 12 extends along the endocardial line 111 at a distance d2 therefrom.

3) Vertical lines (horizontal lines in FIG. 3) $10_k$ (k=0 to n, where n represents the number of divisions) are drawn at intervals d1, starting from the cardiac apex (the tip portion 210 shown in FIG. 1), in the depth direction (the downward direction in FIG. 3). Calculation is performed under the assumption that the acoustic field intensity is constant within a region sandwiched between two adjacent vertical lines drawn at the interval d1. Therefore, the vertical lines 10 will be referred to as "equi-sound-intensity contours" or simply referred to as "acoustic field lines." Regions surrounded by the endocardial line 111, the inner line 11, the outer line 12, and the acoustic field lines 10 are calculation regions. An average intensity $A_k$ of a region (myocardium calculation region) surrounded by the endocardial line 111, the outer line 12, the acoustic field line $10_k$, and the acoustic field line $10_{k+1}$ and an average intensity $B_k$ of a region (cardiac chamber calculation region) surrounded by the endocardial line 111, the inner line 11, the acoustic field line $10_k$, and the acoustic field line $10_{k+1}$ are obtained.

Figure 4:
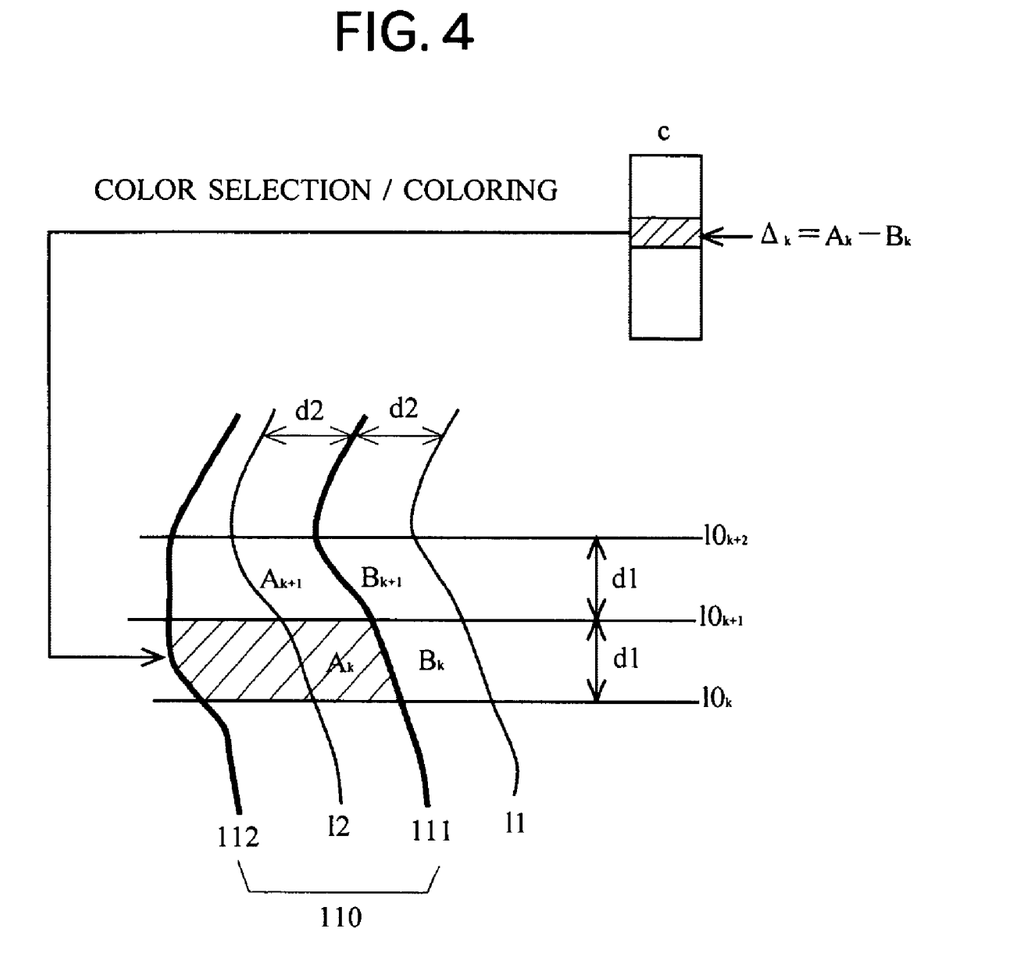
FIG. 4 is a cross sectional view of the heart (the myocardium and the cardiac chamber) to be used for explaining a coloring method used in the equal-interval sliding window method of the present invention.

4) The difference $\Delta_k$ in intensity between the myocardium calculation region and the cardiac chamber calculation region is calculated as follows.

$$\Delta_k = A_k - B_k$$

where $A_k$ represents the average intensity of the myocardium calculation region, and $B_k$ represents the average intensity of the cardiac chamber calculation region. A color corresponding to the difference $\Delta_k$ is selected from a color table c, and the entirety of a myocardium image region sandwiched between the acoustic field line $10_k$ and the acoustic field line $10_{k+1}$ is colored with the selected color. A hatched area in FIG. 4 represents the myocardium image region colored with the selected color.

5) The above steps are repeated, while the calculation regions are shifted (in increments of one region in the vertical direction in FIG. 3), so as to calculate the difference and to color the corresponding myocardium image region, until the entire myocardium image region is colored.

Figure 5:
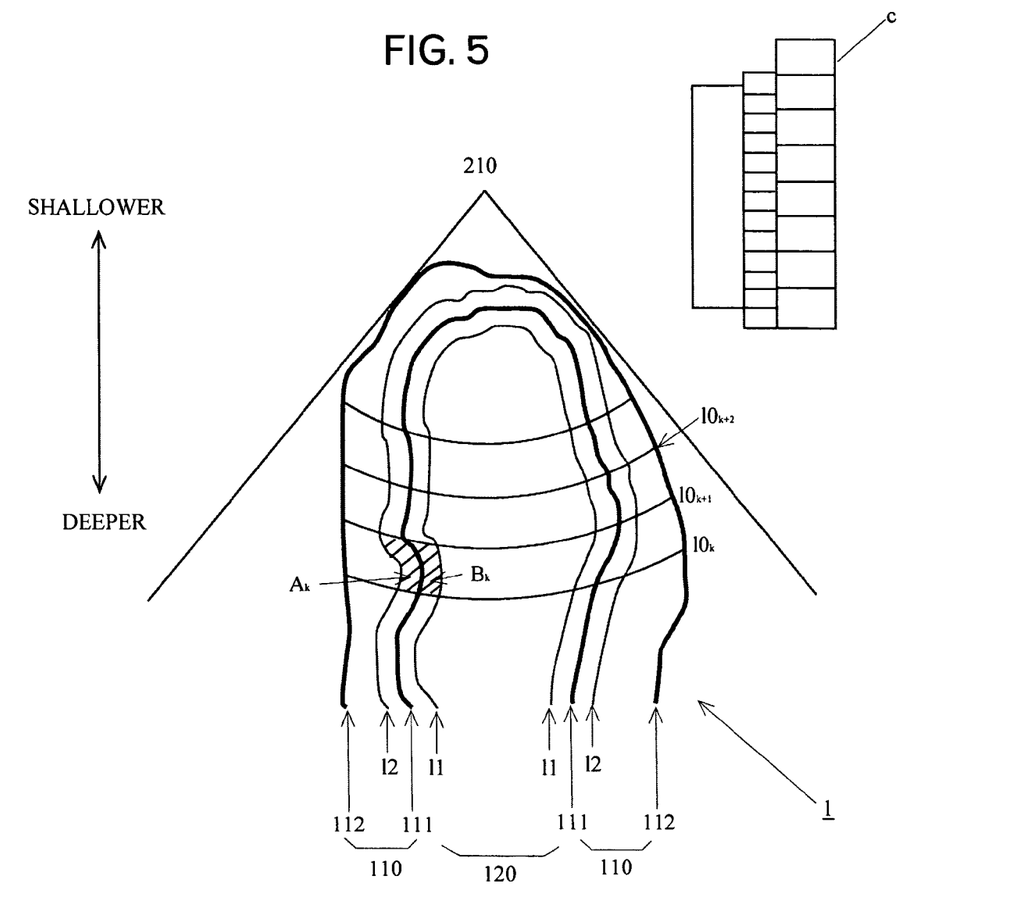
FIG. 5 is a cross sectional view of the heart (the myocardium and the cardiac chamber) to be used for explaining an equal-interval sliding window method of the present invention (an example in which the heart is equally divided in the depth direction by use of arcs)

In the present embodiment, the interval d1 is set to 1 mm to 20 mm, and the distance d2 is set to 1 mm to 20 mm. The reason why the interval d1 is set to 1 mm to 20 mm is that the acoustic field intensity can be considered constant within each of regions formed through division at the intervals d1. As shown in FIG. 1, equi-sound-intensity contours are represented by arcuate lines 10 centered at the tip portion 210. However, in the example shown in FIG. 3, the equi-sound-intensity contours are approximated by straight lines. When the acoustic field intensity in each region is required to have a higher level of uniformity, as shown in FIG. 5, an echo image is divided depthwise by use of arcuate lines centered at the tip portion 210. Since calculation regions ($A_k$ and $B_k$) to be compared with each other are narrow and adjacent to each other, no practical problem arises even when each region surrounded by straight lines is assumed to have a uniform acoustic field intensity. However, since the region in the vicinity of the cardiac apex (the tip portion 210) has a large area, as shown in FIG. 3, the cardiac apex region is divided into n subregions by radial lines extending outwardly from a point 0. FIG. 3 shows an example in which the cardiac apex region is divided into 4 to 8 subregions. In this case, the difference $\Delta_{nj}$ between the intensity $A_{nj}$ of a subregion in the myocardium calculation region and the intensity $B_{nj}$ of a corresponding subregion in the cardiac chamber calculation region is calculated as follows.

$$\Delta_{nj} = A_{nj} - B_{nj} \ (j=1 \text{ to } 4)$$

Figure 6:
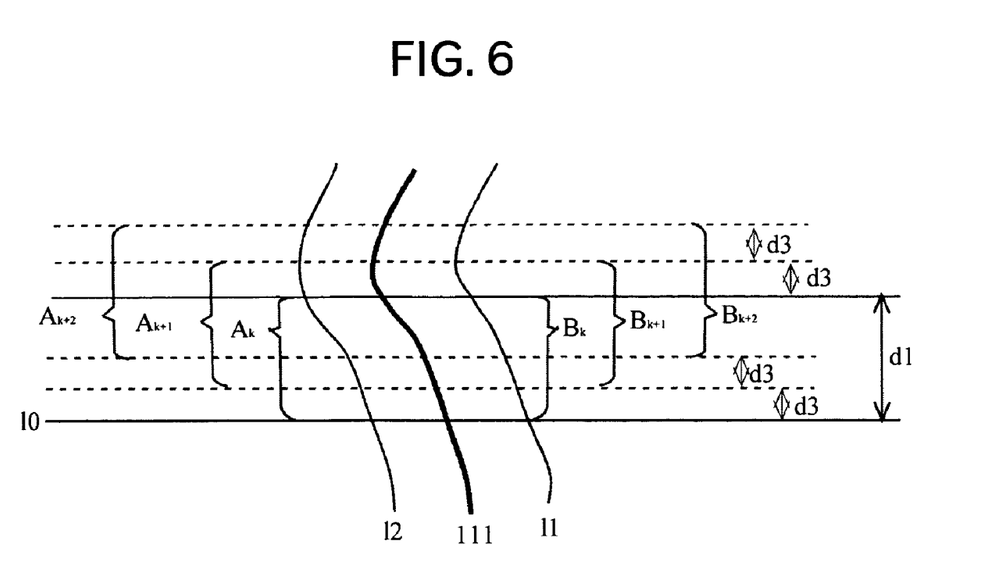
FIG. 6 is a cross sectional view of the heart (the myocardium and the cardiac chamber) to be used for explaining a coloring method used in an overlap sliding window method of the present invention.

Next, an overlap sliding window method will be described. Although the overlap sliding window method is basically identical with the equal-interval sliding window method, it differs from the equal-interval sliding window method in the manner of sliding of calculation regions. Specifically, as shown in FIG. 6, the myocardium and cardiac chamber calculation regions are determined in the same manner as in the equal-interval sliding window method; however, the calculation regions are shifted along the endocardial line 111 in increments of a small distance d3 (e.g. 1 mm). This enables fine correction of a variation in acoustic field intensity in the depth direction.

The reason why the depthwise dimension of each calculation region is not set to the distance d3 is to eliminate influence of noise as described in the summary section (when generation of noise occurs locally, influence of such noise can be suppressed through averaging of image data in a region of a large area (although the area measures 20×20 mm at most)). In the illustrated example, the calculation is started from the deepest calculation regions. However, the calculation may be started from the shallowest calculation regions. This is a matter of programming, and the present invention encompasses both cases.

The reason why the color of a myocardium image region between adjacent acoustic field lines is determined through calculation performed for a corresponding myocardium calculation region in the vicinity of the endocardial line 111 is as follows. As described previously, in some cases the image is not clear in the vicinity of the epicardial, and a blood perfusion disorder tends to occur from the vicinity of the endocardial. Therefore, a blood perfusion disorder can be determined even when the color of a myocardium image region between adjacent acoustic field lines is determined in the above-described manner.

Figure 7:
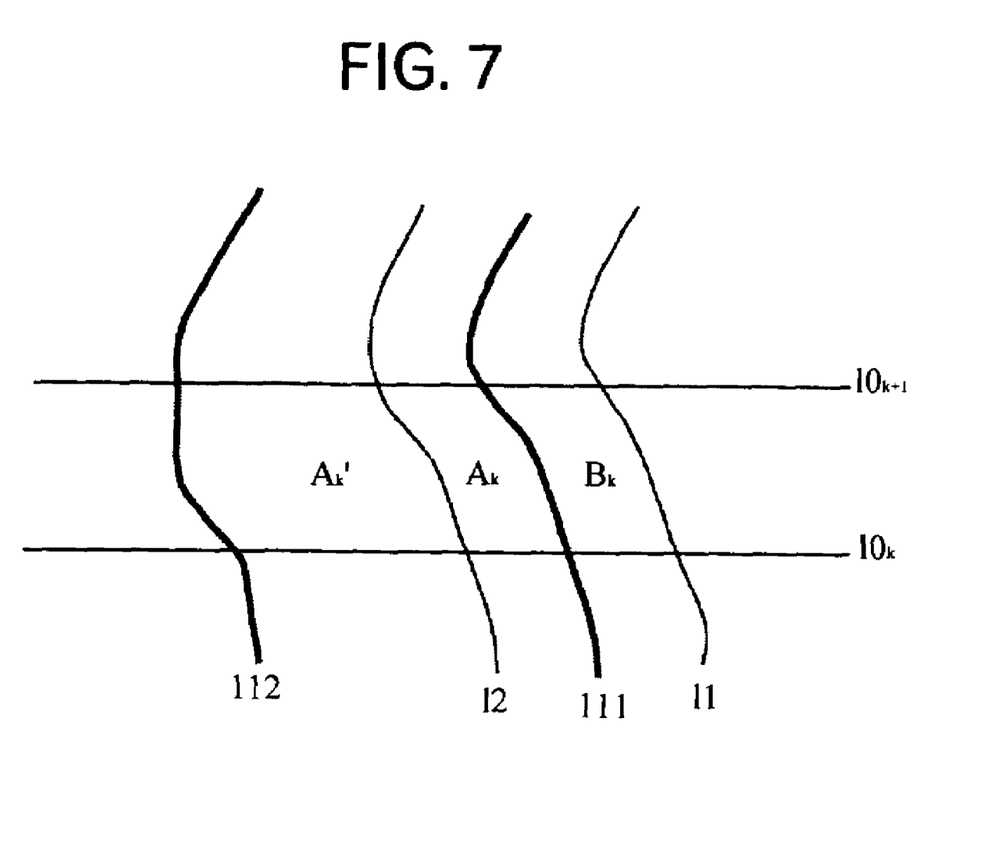
FIG. 7 is a cross sectional view of the heart (the myocardium and the cardiac chamber) to be used for explaining another example of the sliding window method of the present invention in which, for the sake of finer coloring, the myocardium is finely divided into small calculation regions.

However, as shown in FIG. 7, each myocardium image region between adjacent acoustic field lines may be divided into two regions; i.e., an endocardial subregion ($A_k$) and an epicardial subregion ($A_k'$), and calculation for coloring may be individually performed for each of the endocardial subregion ($A_k$) and the epicardial subregion ($A_k'$). Moreover, each myocardium image region between adjacent acoustic field lines may be finely divided into subregions along the thickness direction of the myocardium (the horizontal direction in FIG. 7). In either case, the intensity of each subregion is compared with the intensity $B_k$ of the cardiac chamber calculation region in order to obtain an intensity difference.

Figure 8:
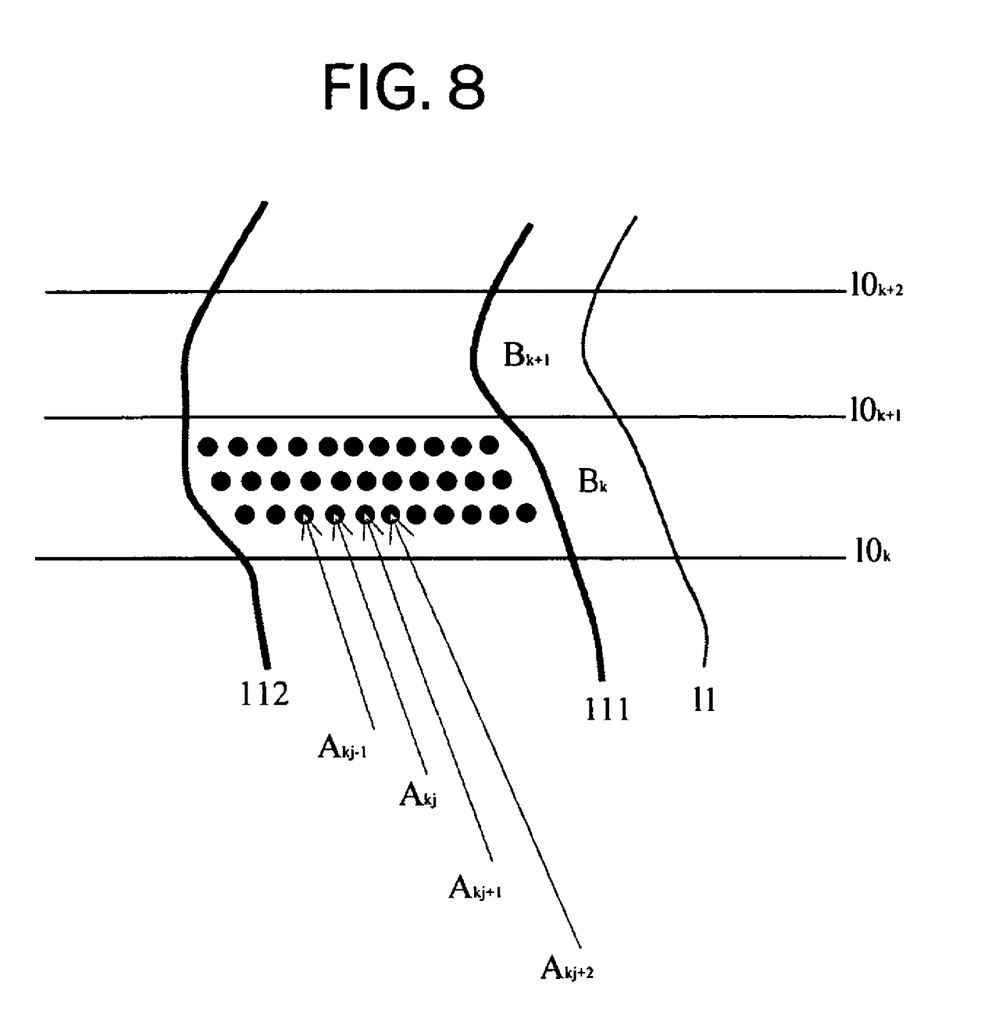
FIG. 8 is a cross sectional view of the heart (the myocardium and the cardiac chamber) to be used for explaining a pixel-by-pixel method of the present invention.

Next, a pixel-by-pixel method will be described. As to a method of determining calculation regions, the pixel-by-pixel method is basically identical with the equal-interval sliding window method; however it differs from the equal-interval sliding window method in that each myocardium calculation region is expanded to extend between the endocardial and the epicardial, and that difference calculation is performed on the pixel-by-pixel basis. FIG. 8 shows calculation regions defined in the pixel-by-pixel method. Although each cardiac chamber calculation region is the same as that defined in the equal-interval sliding window method, a corresponding myocardium calculation region is a region surrounded by corresponding acoustic field lines $10_k$ and $10_{k+1}$, the endocardial line 111, and the epicardial line 112. A calculation for coloring is individually performed for each pixel within the expanded myocardium calculation region. The difference $\Delta_{kj}$ in intensity between each pixel in the myocardium calculation region and the cardiac chamber calculation region is calculated as follows.

$$\Delta_{kj} = A_{kj} - B_k$$

where $A_{kj}$ represents the intensity of the j-th pixel in the myocardium calculation region, and $B_k$ represents the average intensity of the cardiac chamber calculation region. A color corresponding to the difference $\Delta_{kj}$ is selected from the color table, and the j-th pixel in the myocardium calculation region is colored by the selected color. This enables a diagnostician to accurately determine the state of the myocardium on the basis of color. However, when the myocardium calculation region contains noise, noise affects calculation for corresponding pixels, and these pixels are colored accordingly.

Figure 9:
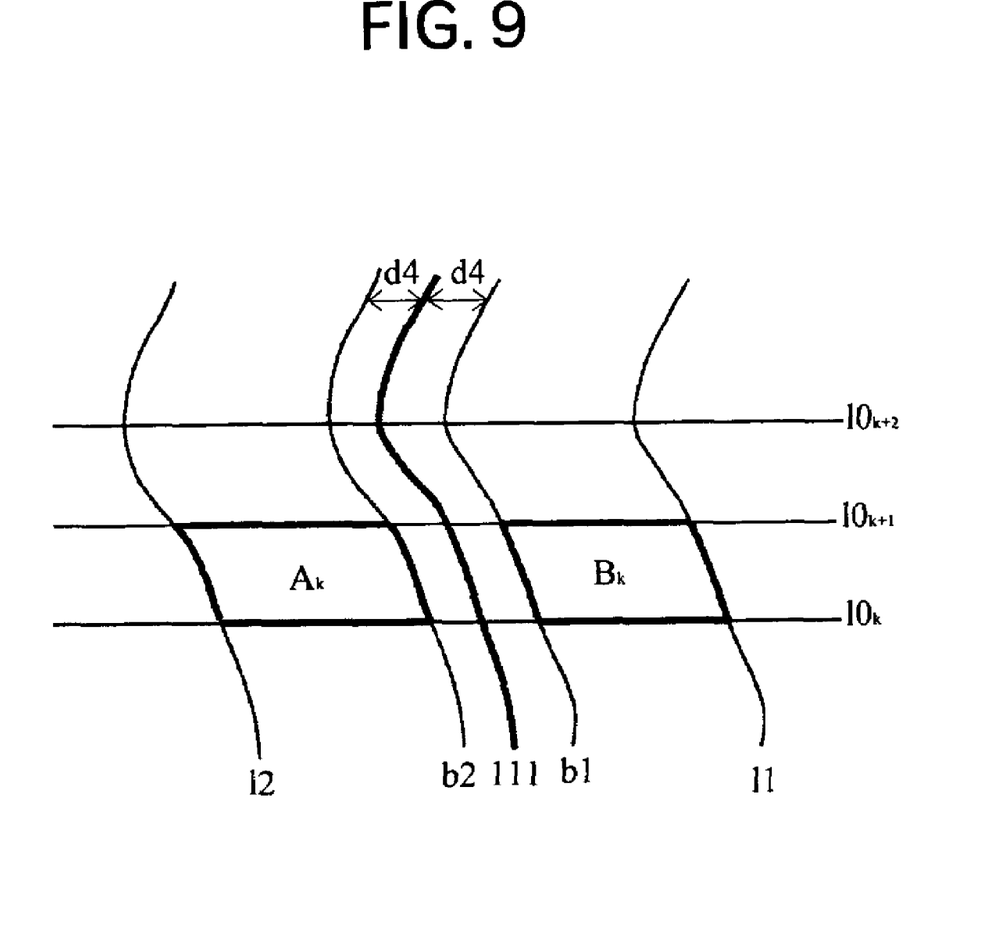
FIG. 9 is a cross sectional view of the heart (the myocardium and the cardiac chamber) to be used for explaining a method of eliminating color-bled portions from calculation regions, which method is used in the coloring method of the present invention.

Above, three coloring methods have been described. Incidentally, in a color image obtained by, for example, the power mode method, there occurs blooming, which is a phenomenon that color of a cardiac chamber image region blooms into a myocardium image region while passing through the endocardial line. Therefore, influence of such color blooming must be eliminated. In the present invention, as shown in FIG. 9, buffer lines b1 and b2 are drawn on the inner side and outer side, respectively, of the endocardial line 111 in such a manner that each of the buffer lines b1 and b2 extends along the endocardial line 111 while being separated from the endocardial line 111 by a distance d4. A region surrounded by corresponding acoustic field lines $10_k$ and $10_{k+1}$, the buffer line b1, and the inner line 11 is defined as a cardiac chamber calculation region, and a region surrounded by corresponding acoustic field lines $10_k$ and $10_{k+1}$, the buffer line b2, and the outer line 12 is defined as a myocardium calculation region. Thus, influence of blooming can be eliminated. Needless to say, in the case of the pixel-by-pixel method, the myocardium calculation region extends between the buffer line b2 and the epicardial line. Notably, the value of the distance d4 can be adjusted; specifically, increased and decreased in increments of 0.5 mm, and the buffer lines b1 and b2 are automatically depicted on the basis of the adjusted value of the distance d4.

Figure 10:
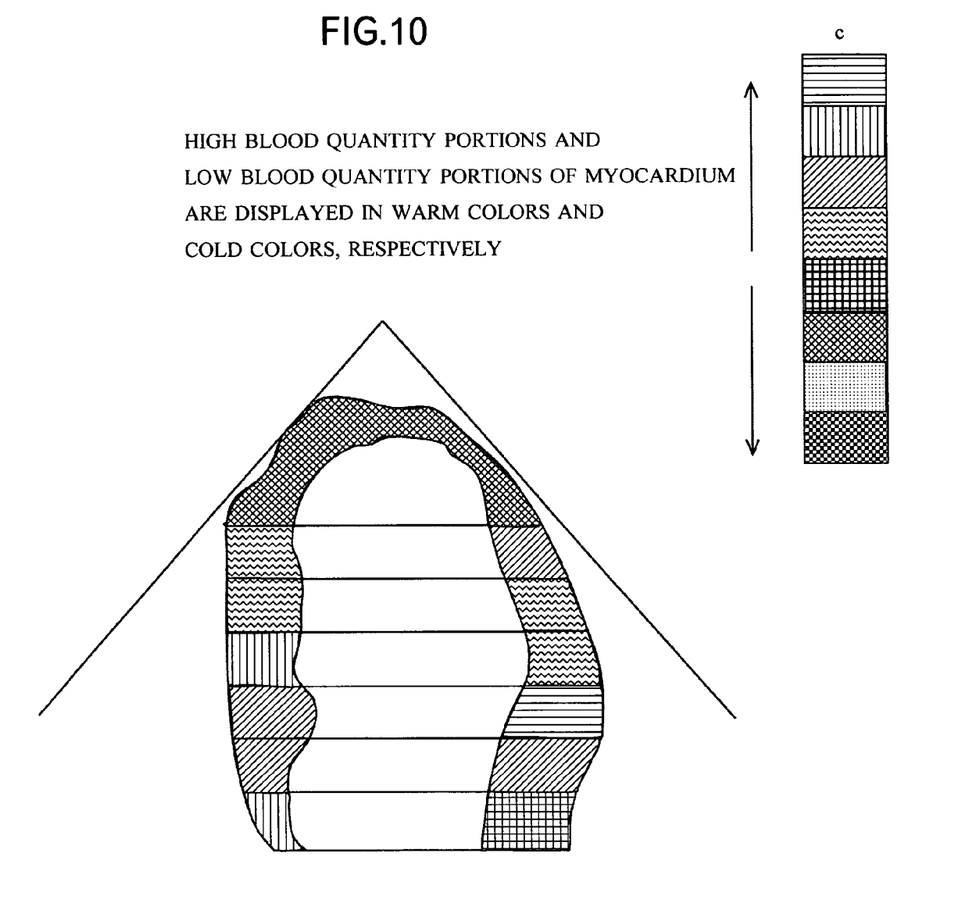
FIG. 10 is a diagram showing an image of the heart (the myocardium and the cardiac chamber) colored by the coloring method of the present invention.

FIG. 10 shows an image of the heart colored by the above-described method. Colors of subregions in the myocardium image region represent the state of blood perfusion within the myocardium. The darker the color, the worse the perfusion state. Accordingly, a diagnostician can graph the state of perfusion by viewing the colored image.

The above-described coloring methods enable visual indication of the blood perfusion state. However, numerical indication of the blood perfusion state is also possible. That is, actual blood volume can be calculated as follows.

First, the power P of a region of interest of a contrast echo image is determined. The power P represents a ratio of the blood volume in the myocardium to the blood volume (100 ml/100 g) in the cardiac chamber (during actual observation, intensity is measured; however, intensity can be treated as blood volume, because intensity is proportional to microbubble concentration, which is proportional to blood volume). The power P can be obtained from the following equation:

$$10 \log_{10} P = I_1 - I_2 \qquad \text{Eq. 1}$$

where $I_1$ represents the intensity of the myocardium image region, $I_2$ represents the intensity of the cardiac chamber myocardium image region, which can be obtained from the region of interest of the contrast echo image. $I_1$ and $I_2$ correspond to the above-described $A_k$ and $B_k$, respectively.

Accordingly, the blood volume V (unit: ml/100 g) in the myocardium in the region of interest in an ordinary state can be calculated as follows:

$$V = 100 \times P \text{ (ml/100 g)}$$

For example, in the case where the intensity difference $\Delta = -10$ dB ($\Delta = I_1 - I_2$), from Equation 1, the power P can be obtained as follows.

$$P = \frac{1}{10}$$

Therefore, the blood volume V in the region of interest can be obtained as follows.

$$V = 100 \cdot P = 10 \text{ ml/100 g}$$

Since the blood volume in the myocardium is less than that in the cardiac chamber, the thus-obtained blood value V is normal.

Diagnosing blood perfusion within the myocardium from a contrast echo image requires a high level of skill and experience, and is difficult even for a medical specialist. In addition, such a contrast echo image involves various problems such as inclusion of noise, depthwise attenuation of acoustic field intensity (intensity of ultrasound waves), and increased intensity in the vicinity of a focal point. However, since conventional analysis methods have not taken these problems into consideration, blood perfusion diagnosis has depended heavily on experience.

The present invention has solved the above-described problems by obtaining the difference between the intensity of a cardiac chamber image region and the intensity of a myocardium image region, which regions have the same acoustic field intensity. Specifically, even when the acoustic field intensity attenuates depthwise or locally increases in the vicinity of the focal point, problems attributable to variations in intensity among locations caused by the attenuation and local increase are solved by calculating the difference in intensity between a cardiac chamber image region and a myocardium image region, which regions have the same acoustic field intensity and serve as calculation regions. Moreover, the problem of local noise generation is solved by obtaining the average intensity of each calculation region (narrow region which is considered to have generally a uniform acoustic field intensity). Furthermore, the problem of color bleeding which would otherwise occur in a color image produced by the power mode method is solved through provision of buffer lines. For these reasons, a colored image of the myocardium obtained in accordance with the analysis method of the present invention enables a diagnostician to easily grasp the state of blood perfusion in the myocardium by observing the colored image of the myocardium. This is because colors in the color table represent different degrees of blood perfusion.

When the above-described analysis is to be performed, a diagnostician (usually, a doctor) is required to draw an endocardial line and an epicardial line of the myocardium, which, however, is a simple step. The remaining steps are performed by means of a program. Therefore, any person can easily use the analyzing method and can determine the state of blood perfusion in the myocardium. Use of the blood volume calculation equation of the present invention enables quantitative determination of the state of blood perfusion in the myocardium, because the blood volume at the region of interest can be obtained in the form of a numerical value.

The present invention provides three coloring methods; i.e., the equal-interval sliding window method, the overlap sliding window method, and the pixel-by-pixel method. In the sliding window methods, the state of blood perfusion in the vicinity of the endocardial is represented by use of colors. Use of the equal-interval sliding window method realizes high calculation speed. Use of the overlap sliding window method realizes continuous representation of the state of blood perfusion in the myocardium. In the sliding window methods, each myocardium image region between acoustic field lines is colored in accordance with the state of blood perfusion in the vicinity of the endocardial. However, as described in relation to the above embodiment, when each calculation region is finely divided along the thickness direction of the myocardium (the direction from the endocardial toward the epicardial) for calculation of intensity differences, the state of blood perfusion, which may vary in the direction from the endocardial toward the epicardial, can be accurately displayed.

However, as described previously, in some cases a clear image is not obtained in the vicinity of the epicardial. Therefore, at the present time, the sliding window methods, which color each myocardium image region in accordance with the intensity difference of a corresponding calculation region in the vicinity of the endocardial, raise no practical problems. Specifically, a blood perfusion disorder tends to occur from the vicinity of the endocardial, and therefore, when the vicinity of the endocardial is analyzed accurately, no significant medical problem arises.

The pixel-by-pixel method does not involve the above-described problems, because the entirety of a myocardium image region is evaluated on the pixel-by-pixel basis. That is, an original contrast echo image can be evaluated accurately from the endocardial to the epicardial. However, since a portion of the myocardium image region containing noise or an unclear portion in the vicinity of the epicardial is evaluated as it is for coloring, the pixel-by-pixel method cannot be said to be superior to the sliding window methods at the present. Therefore, the pixel-by-pixel method can be effectively used as a method for fine evaluation when a contrast echo image which does not contain noise and which is clear to the vicinity of the epicardial is obtained.

Once a contrast echo image is available (is obtained), the analysis-display method of the present invention can be practiced by use of a commonly used personal computer. Therefore, any person can introduce the analysis-display method in the form of low-cost image analysis software. Further, since operation is very simple, the analysis-display method is an effective tool for doctors who are unaccustomed to using personal computers.

Obviously, numerous modifications and variations of the present invention are possible in light of the above teachings. It is therefore to be understood that within the scope of the appended claims, the present invention may be practiced otherwise than as specifically described herein.

What is claimed is:

1. A blood-volume analysis-display method of analyzing a contrast echo image of the myocardium and a cardiac chamber so as to determine and display the volume of blood within the myocardium, the contrast echo image being obtained by use of ultrasound diagnostic equipment after injection of a microbubble ultrasound contrast agent into blood vessels, and including a myocardium image region corresponding to the myocardium and a cardiac chamber image region corresponding to the cardiac chamber, the method comprising:
   (a) finely dividing the contrast echo image into a plurality of calculation regions, each being considered to have a uniform acoustic field intensity and covering a portion of the myocardium image region and a corresponding portion of the cardiac chamber image region;
   (b) obtaining, for each calculation region, a difference in intensity between the myocardium image region and the cardiac chamber image region, and determining the volume of blood within the myocardium on the basis of the difference; and
   (c) coloring the myocardium image region in accordance with the determined blood volume.

2. A blood-volume analysis-display method according to claim 1, wherein
   for each calculation region, a power P is first obtained by the following equation:

$$10 \log_{10} P = I_1 - I_2$$

where $I_1$ represents the intensity of the myocardium image region, $I_2$ represents the intensity of the cardiac chamber image region; and
   subsequently, a blood volume V (unit: ml/100 g: blood volume) in the myocardium is calculated by the following equation:

$$V = 100 \times P \text{ (ml/100 g)}.$$

3. A blood-volume analysis-display method according to claim 1, comprising:
   (a) tracing the endocardial and the epicardial to thereby form an endocardial line and an epicardial line, respectively;
   (b) drawing an inner line and an outer line on the inner and outer sides, respectively, of the endocardial line in such a manner that each of the inner line and the outer line extends along the endocardial line while separated therefrom by a predetermined distance;
   (c) drawing two boundary lines at a predetermined interval in the depth direction in order to obtain a region that is considered to have a uniform acoustic field intensity;
   (d) defining a cardiac chamber calculation region, which is a region surrounded by the endocardial line, the inner line, and the boundary lines, and a myocardium calculation region, which is a region surrounded by the endocardial line, the outer line, and the boundary lines;
   (e) subtracting the average intensity of the cardiac chamber calculation region from the average intensity of the myocardium calculation region to thereby obtain a luminous difference;
   (f) selecting a color corresponding to the luminous difference from a color table, and coloring with the selected color the entirety of a myocardium image region sandwiched between the acoustic field lines; and
   (g) repeating the steps (c) to (f), while shifting the boundary lines in the depth direction by a shifting distance not greater than the predetermined interval.

4. A blood-volume analysis-display method according to claim 3, wherein the shifting distance is a smaller than the predetermined interval.

5. A blood-volume analysis-display method according to claim 4, wherein the shifting distance is about one tenth of the predetermined interval.

6. A blood-volume analysis-display method according to claim 1, comprising:
   (a) tracing the endocardial and the epicardial to thereby form an endocardial line and an epicardial line, respectively;
   (b) drawing an inner line on the inner side of the endocardial line in such a manner that the inner line extends along the endocardial line while separated therefrom by a predetermined distance;
   (c) drawing two boundary lines at a predetermined interval in the depth direction in order to obtain a region that is considered to have a uniform acoustic field intensity;
   (d) defining a cardiac chamber calculation region, which is a region surrounded by the endocardial line, the inner line, and the boundary lines, and a myocardium calculation region, which is a region surrounded by the endocardial line, the epicardial line, and the boundary lines;
   (e) calculating the difference between the intensity of each pixel within the myocardium calculation region and the average intensity of the cardiac chamber calculation region to thereby obtain a luminous difference for each pixel, and coloring each pixel with a color corresponding to the luminous difference, the color being selected from a color table; and
   (f) repeating the steps (c) to (e), while shifting the boundary lines in the depth direction by a shifting distance not greater than the predetermined interval.

7. A blood-volume analysis-display method according to claim 3, further comprising:
   drawing first and second buffer lines on the inner side and outer side, respectively, of the endocardial line in such a manner that each of the buffer lines extends along the endocardial line while being separated from the endocardial line by a predetermined distance; and
   defining, as the cardiac chamber calculation region, a region surrounded by the boundary lines, the first buffer line, and the inner line; and
   defining, as the myocardium image region, a region surrounded by the boundary lines, the second buffer line, and the outer line.

* * * * *